United States Patent [19]

Imbert

[11] 4,344,192
[45] Aug. 17, 1982

[54] FULL DUAL ELEMENT PROSTHESIS DESIGNED FOR THE FEMORO-PATELLAR JOINT

[76] Inventor: Jean C. Imbert, Les Flaches, Route de St Heand, 42580 l'Etrat, France

[21] Appl. No.: 168,137

[22] Filed: Jul. 14, 1980

[51] Int. Cl.³ ............................................... A61F 1/24
[52] U.S. Cl. ..................................... 3/1.91; 128/92 C
[58] Field of Search ...................... 3/1.91, 1.911, 1.9, 3/1.913; 128/92 C

[56] References Cited

U.S. PATENT DOCUMENTS

| | | | |
|---|---|---|---|
| 3,806,961 | 4/1974 | Muller | 3/1.91 X |
| 4,151,615 | 5/1979 | Hall | 3/1.91 |
| 4,156,944 | 6/1979 | Schreiber | 3/1.91 |
| 4,178,641 | 12/1979 | Grundei et al. | 3/1.911 |

Primary Examiner—Ronald L. Frinks
Attorney, Agent, or Firm—Remy J. VanOphem

[57] ABSTRACT

Full dual element prosthesis designed for the femoro-patellar joint. This invention pertains to a full dual element prosthesis for the femoro-patellar joint, and including a dissymmetrical patellar support.

A piece, including a convex surface 24 and attached inside the patella 3, is resting against a tapered surface 28 which is attached to the femur 2 by a lug 29. The surface 28 is perpendicular to the direction of the resulting contact force 13.

This full dual element prosthesis is designed for the treatment of the femoro-patellar lesions.

6 Claims, 16 Drawing Figures

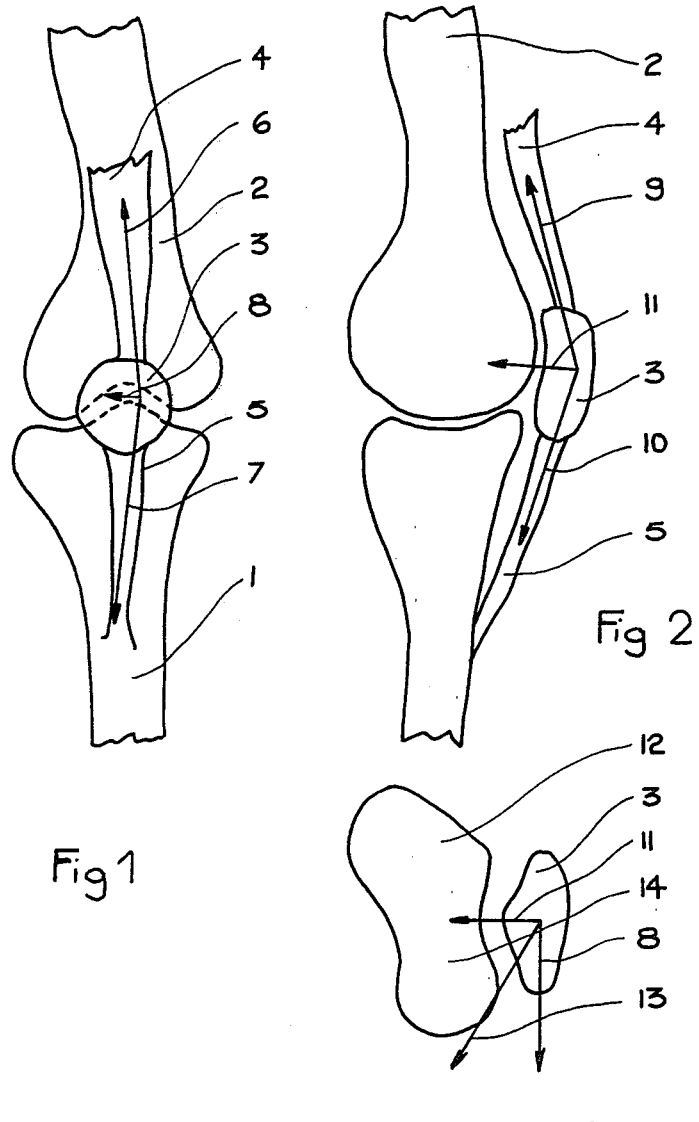

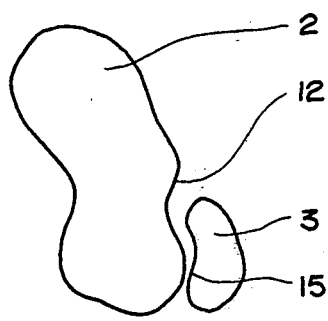
Fig 4
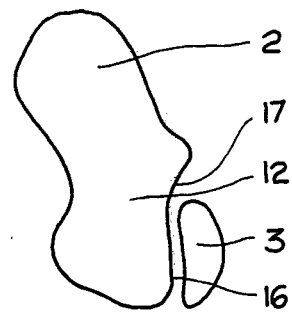
Fig 5
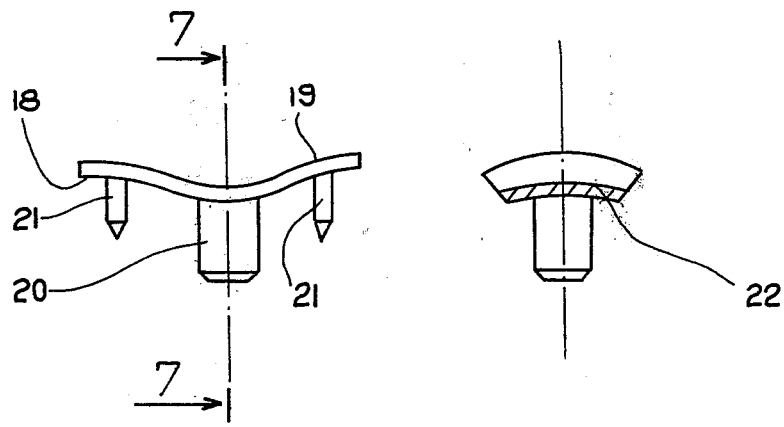
Fig 6
Fig 7

Fig 8
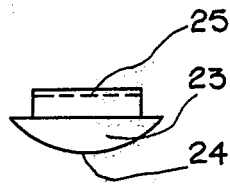
Fig 9
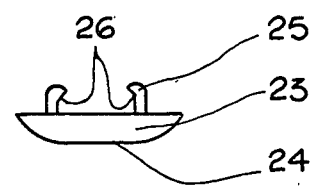
Fig 10
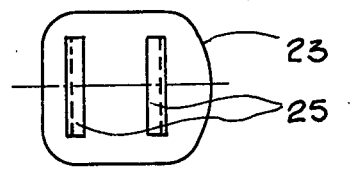
Fig 11
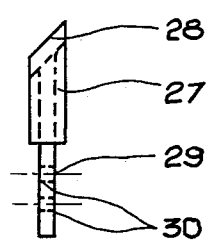
Fig 12
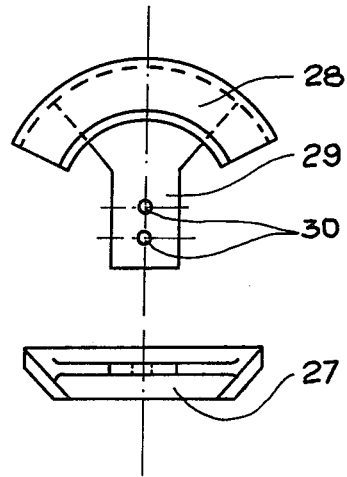
Fig 13

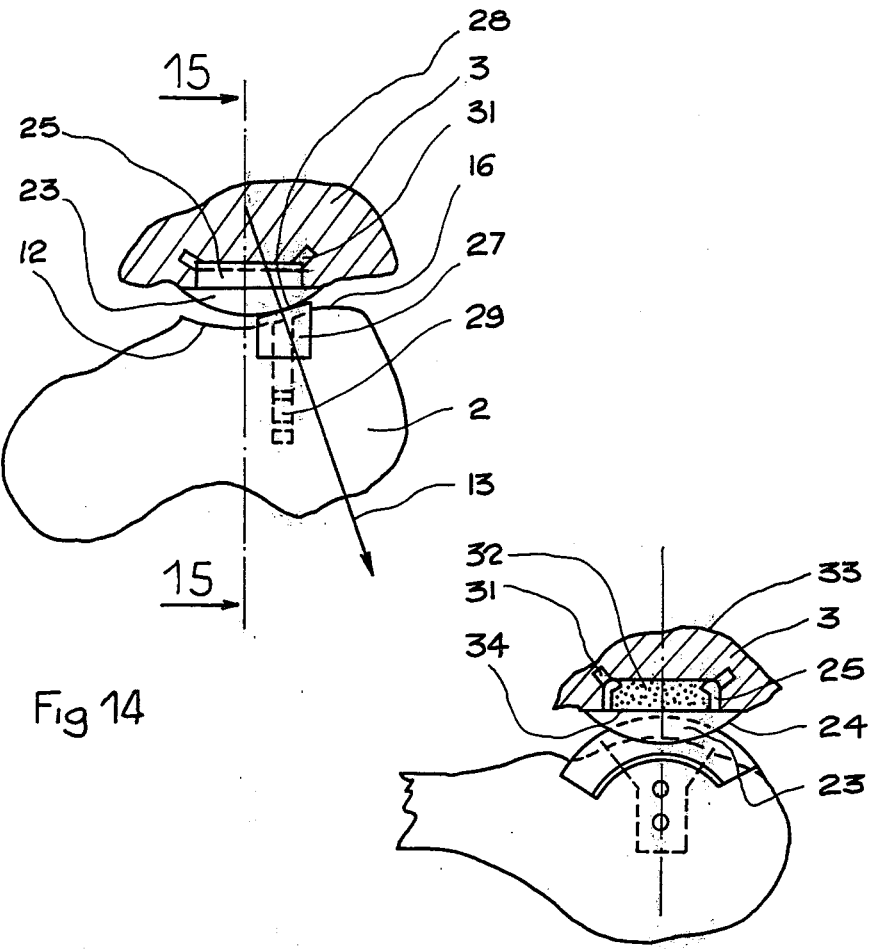
Fig 14
Fig 15
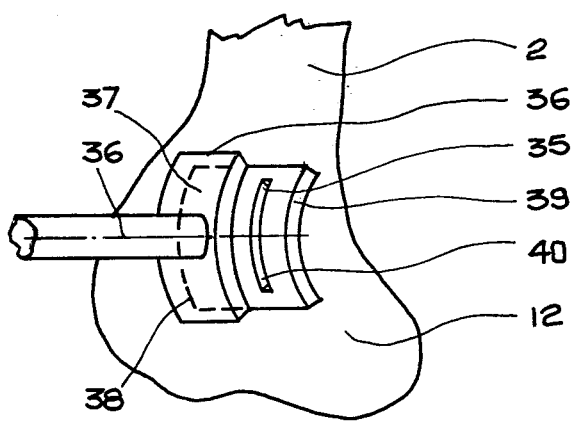
Fig 16

FULL DUAL ELEMENT PROSTHESIS DESIGNED FOR THE FEMORO-PATELLAR JOINT

BACKGROUND OF THE INVENTION

The present invention pertains to a surgical prosthesis designed to remedy the cartilage wear in the patella and femoral trochlea of the human knee.

The knee includes the femoro-tibial joint, as well as the femoro-patellar joint.

The upper part of the patella is continued by the quadriceps and the lower part is connected to the tibia by the patellar tendo. The patella is connected with the femur, on its lower and external sides, by the marsupia patellaria.

Under the combined efforts produced from the quadriceps, the patellar tendo and the marsupia patellaria, the patella is subjected to an effort applied on the femur, and more particularly on the cartilage of the femoral trochlea.

Cartilage wear can therefore be noticed in the patella or the femoral trochlea of various individuals. The well known Mac Keever prosthesis is a partial prosthesis and consists of a kind of metal shell designed to cover the rear side of the patella, while sliding against the trochlear cartilage.

The femoro-patellar options offered by the Freeman and Gunston prosthesis are also well known.

Another popular model is the Bechtol full prosthesis, which is a symmetrical prosthesis including a metal trochlear element and a polyethylene patellar element with tilt adjustable edges.

The disadvantage of these types of prosthesis is that they cannot be adapted to the case of isolated femoro-patellar arthrosis with fixed, partial dislocation of the patella. Indeed, the treatment of this lesion requires four conditions which consist of the surface replacement, the alignment of the patella with the femur, the adaptation of the prosthesis to the deformation of the osseous parts concerned and the provision for a sufficient, undamaged spot in case of failure, so as to make a correction possible.

Some well-known prosthesis meet the first two requirements, but their adaptation to the sometimes significant deformations of the trochlea may be uneasy; moreover, in case of failure, their removal may reveal a surface which is damaged to the point that the efforts produced by the quadricipital tendo, following patellectomy, may no longer be tolerated. These disadvantages are suppressed by the present invention inasmuch as the device adapts itself to the deformation of the osseous parts.

SUMMARY OF THE INVENTION

According to another specification of the invention, the prosthesis consists of two elements, namely a plastic trochlear rail which is applied on the worn side of the femoral trochlea, and a metal patellar piece, affixed to the worn part of the patella which is in direct contact with the femoral trochlea.

According to another specification of the invention, the plastic trochlear rail being applied on the sole worn side of the trochlea, and not on both sides, allows for the strict observance of the functional asymmetry of the said trochlea.

BRIEF DESCRIPTION OF THE DRAWINGS

The schematic, attached drawings will give a better understanding of the invention specifications.

FIG. 1 is a front elevation of the femoral-tibial joint and of the patella, showing the efforts that are exercised along the foreplane of the latter.

FIG. 2 is a left hand side view of the joint illustrated on FIG. 1, and showing the efforts which are exercised on the patella, in the antero-posterior plane.

FIG. 3 is a lower view of the joint represented on FIG. 2 and showing the direction of the force resultant exercised upon a patella.

FIG. 4 shows a patella wear variation.

FIG. 5 shows a trochlea wear variation.

FIG. 6 is a front elevation of a popular trochlear prosthesis.

FIG. 7 is a cross-section, following A—A, of the prosthesis shown on FIG. 6.

FIG. 8 is an elevation of the patellar piece designed to the specifications of the invention.

FIG. 9 is a left hand side view of the patellar piece designed to the specifications of the invention, and represented on FIG. 8.

FIG. 10 is a top view of the patellar piece designed according to the invention's specifications.

FIG. 11 is an elevation view of the trochlear rail following the invention.

FIG. 12 is a left hand side view of that rail designed to the specifications of the invention.

FIG. 13 is a lower view of the rail built to the specifications of the invention.

FIG. 14 is an elevation view of the positioning of both parts of the prosthesis designed to the specifications of the invention, and set in operating position.

FIG. 15 is a cross-section, following X—X, (FIG. 14), of the prosthesis assembly designed to the specifications of the invention, and set in operating position.

FIG. 16 illustrates the positioning gauge of the invented trochlear rail attaching notch.

DETAILED DESCRIPTION OF THE PREFERRED EMBODIMENT

FIG. 1 illustrates the femoro-patellar joint including the tibia 1, the femur 2 and the patella 3.

The patella 3 is held in position by the quadriceps 4 and the patellar tendo 5.

The effort produced by the quadriceps 4 is applied onto the patella 3, following the direction indicated by arrow 6.

The effort produced by the patellar tendo 5 is applied onto the patella 3, following the direction indicated by arrow 7.

It should be noted that forces 6 and 7 are not directly opposed and that they define a wide angle on the external side of the joint; both of these forces also define a resulting force called subluxating force 8 which is applied onto the patella and directed outward of the joint.

FIG. 2 illustrates the femoro-patellar joint as seen from the side. The quadriceps 4 exercises a force directed following arrow 9 on the patella 3.

The patellar tendo 5 exercises a force directed as indicated by arrow 10 on the patella 3.

It should be noted that forces 9 and 10 are not directly opposed, and that they define a wide angle in the back of the knee, thus defining a resulting force 11 also called patellar applied force; applied onto the patella 3, that force is directed against the femur 2.

FIG. 3 is a top view of the femoro-patellar joint. The patella 3 is subjected to force 11, applied on the patella and directed against the femoral trochlea 12, and to subluxating force 8, so that the patella 3 is ultimately subjected to resulting force 13 which is directed against the sole side 14 of the femoral trochlea 12.

FIG. 4 illustrates a top view of the femoro-patellar joint including the femur 2 and its trochlea 12, on which the patella 3 is jointed. This Figure illustrates a case of arthrosis affecting the patella 3 whose cartilage 15 shows a significant lesion responsible for a fixed patellar subluxation.

FIG. 5 is a top view of the femoro-patellar joint, including the femur 2 and the trochlea 12 with its banks 16 and 17, and of the patella 3.

The case hereby illustrated is that of the arthrosis of the femoral trochlea whose lateral cartilage 16 reveals a significant lesion causing a fixed patellar subluxation.

FIG. 6 is a front elevation of a popular prior art type of trochlear prosthesis. It includes two banks 18 and 19, designed to be applied against the banks of the femoral trochlea, an attaching pin 20 designed to be attached at the center of the femoral trochlea, and two rotation stop pieces 21 designed to be attached onto the trochlear banks.

FIG. 7 is an A—A cross-section of a popular prior art type of trochlear prosthesis following section A—A. It should be noted that the convex shape of bank 22, designed to be applied to the respective bank of the femoral trochlea, is represented.

FIG. 8 illustrates the metal patellar piece 23, built to the specifications of the invention. This part, designed to be attached to the patella, after elimination of the damaged surfaces, includes a convex element 24 which applies onto the femoral trochlea, and tenons 25 which are used to attach this part into the patella.

FIG. 9 illustrates the patellar part designed according to the invention. Both attaching tenons 25 are represented. Each tenon includes a slanted end 26 so as to provide a better grip on the cement located inside the cavity provided in the patella.

FIG. 10 is a top view of the patellar piece 23 designed according to the invention. This Figure shows the external shape of the lower convex side which is applied against the femoral trochlea.

FIG. 11 is an elevation view of the invented femoral trochlear component which defines a frusto-conical sector portion in plan view consisting of a curved rail 27 having an outer anterior surface portion and an inner posterior surface portion. The outer anterior surface also includes a slanted contact surface 28 which rests against the convex portion 24 of the patellar piece 23. The inner and outer surfaces are bounded by a pair of parallel side edges and oblique angled end edges as shown in FIG. 13. The inner posterior surface portion has a narrow body portion contiguous thereto forming an attaching lug 29 which penetrates into the femur. A number of holes 30 have been provided in the attaching lug 29, so as to let the osseous tissue of the femur penetrate through it, thus reinforcing the attachment of the trochlear rail into the femur.

The attaching lug 29 is substantially parallel to and interposed the pair of parallel side edges of the frusto-conical sector and forms an angle ranging from 20° C. to 25° with the generating line of the outer slanted contact surface 28.

FIG. 12 is a left hand side view of the trochlear rail according to the invention. It should be noted that the contact surface 28 has a round shape, so as to match the curve of the femoral trochlea as observed in the vertical plane.

FIG. 13 is a lower view of the trochlear rail 27 according to the invention.

FIG. 14 illustrates the femoro-patellar joint including the femur 2 and the patella 3. The trochlear rail 27, called for in the invention, has been positioned over bank 16 of the femoral trochlea 12. The patellar piece 23, designed to the specifications of the invention, has been placed over the patella 3. The trochlear rail 27 is attached to the trochlear bank 16 by the attaching lug 29 which penetrates the femur 2. The patellar piece 23 is attached to the patella 3 by the tenons 25 which penetrate into the patella 3. The attachment of the patellar piece 23 is improved by the recesses 31 provided in the patella 3, and designed to be filled with cement. Under the efforts produced by the quadriceps and the patellar tendo, the patellar piece 23 is subjected to a force following the direction indicated by arrow 13, and applied onto the trochlear rail 27 and its contact surface 28. It should be noted that the angle formed by the contact surface 28 of trochlear rail 27 and the patellar piece 23 provides an optimal joint operation, the force applied in the direction of arrow 13 being roughly perpendicular to the contact surface 28.

FIG. 15 is a cross-section X—X (FIG. 14) of the prosthesis assembly. The attaching tenons 25 are placed in a parallelepiped recess 32 filled with cement 33. This cement 33 also fills recesses 31, the assembly allowing for an efficient attachment of patellar piece 23. The face 34 of patella 3 has been levelled in order to allow a good positioning of patellar piece 23.

FIG. 16 is a view of the femur 2 showing the location of the notch 35 on the trochlear rail 27 attaching lug. A gauge 36 is placed against the femoral trochlea 12. The surface 37, limited by the perimeter 38 of gauge 36, is marked for reference. A second gauge 39 is placed against gauge 36. This gauge 39 includes a recess 40 which defines the area of the femoral trochlea to be incised in order to attach the lug 29 of trochlear rail 27. The area limited by gauge 36 shall be left intact.

Having described the invention, I claim:

1. In combination with a prosthetic implant for a knee joint wherein a patellar component has an anterior surface adapted to be secured within a resection in the patella, a posterior surface having a convex portion defining a central axis, a femoral trochlear component having a posterior portion adapted to be secured within a resection of the femur, the improvement comprising:

a frusto-conical sector portion mounted opposite said posterior portion of the femoral trochlear component, said frusto-conical sector portion having an outer surface adapted to communicate with said convex portion of the patellar component defining the anterior surface of the femoral component, an inner surface and a pair of parallel side edges;

said posterior portion of the femoral trochlear component further defining a rail portion extending along said inner surface of the frusto-conical sector portion; a narrowed body portion contiguous said rail portion and means for securing said frusto-conical sector portion within a resection of the femur;

said femoral trochlear component further being sized and shaped for mounting to one bank of the trochlear of the femur a predetermined offset distance from said central axis of the convex portion of the posterior surface of the patellar component such that the resultant force of the forces applied to the patella by the patellar tendo and the quadriceps muscles is directed against and is substantially normal to the anterior surface of the femoral component whereby arthrosis of the femoro-patellar joint are substantially eliminated.

2. The combination as claimed in claim 1 wherein said patellar component further comprises at least two attaching parallel tenons mounted to said anterior surface of the patellar component, said at least two attaching tenons each having a converging end portion such that said converging end portions provide an improved grip on the means used to secure the patellar element within the resection of the patellar.

3. The combination as claimed in claim 2 wherein said converging end portions of the parallel attaching tenons are converging towards each other thereby providing a shorter distance between the converging end portions than between the two parallel sides and enhancing the retention of the patellar element within the resection of the patella.

4. The combination as claimed in claim 1 wherein said narrowed body portion contiguous said rail portion is substantially parallel to and interposed said pair of side edges of the frusto-conical sector, said narrowed body portion further being at an angle ranging from 20° to 25° with a generating line of the outer surface of the frusto conical section.

5. The combination as claimed in claim 1 wherein said narrowed body portion contiguous said rail portion further includes at least one aperture formed therein, such that said aperture provides a substantially improved grip on the means used to secure the patellar element within the resection of the femur.

6. A method of replacing a patellar-femoral joint with a prosthetic patellar-femoral joint comprising the steps of:
resecting the posterior surface of the patella;
filling said recess with cement;
placing a patellar prosthetic component having two attaching parallel tenons with converging end portions in the resected portion of the patella;
the dimensions of the resected portion of the patella adapted to receive said two attaching parallel tenons;
placing a gage against the femoral trochlea;
marking the periphery of the gage placed against the femoral trochlea;
placing a second gage contiguous to said first gage against the femoral trochlea;
said second gage including a recess defining the periphery of the resection to be made in the femoral trochlea;
marking the periphery of said recess in the second gage on the femoral trochlea;
resecting the anterior surface of the femoral trochlea, said resected area corresponding to the periphery of the recess in the second gage as marked on said femoral trochlea;
filling said resected portion of the femoral trochlea with cement; and
placing a femoral prosthetic component having a rail portion in said resected anterior surface, the dimensions of the resected portion of the femoral trochlea adapted to receive said rail portion of the prosthetic femoral component.

* * * * *

UNITED STATES PATENT AND TRADEMARK OFFICE
CERTIFICATE OF CORRECTION

PATENT NO. : 4,344,192

DATED : August 17, 1982

INVENTOR(S) : Jean Claude Imbert

It is certified that error appears in the above-identified patent and that said Letters Patent is hereby corrected as shown below:

Column 1, line 58, before the word "According" insert --- The invention is a full duel element prosthesis designed for the femoral-patellar joint and includes a dissymmetrical patellar support. ---.

Column 2, line 39, delete "gauge" and insert --- gage ---.

Column 2, line 50, before "arrow" insert --- the ---.

Column 2, line 53, before "arrow" insert --- the ---.

Column 2, line 54, after "that" insert --- the ---.

Column 2, line 60, delete "exercises" and insert --- exercise ---.

Column 2, line 61, after "following" insert --- the ---.

Column 2, line 63, after "by" insert --- the ---.

UNITED STATES PATENT AND TRADEMARK OFFICE
CERTIFICATE OF CORRECTION

PATENT NO. : 4,344,192  Page 2 of 4

DATED : August 17, 1982

INVENTOR(S) : Jean Claude Imbert

It is certified that error appears in the above-identified patent and that said Letters Patent is hereby corrected as shown below:

Column 2, line 64, after "that" insert --- the ---.

Column 3, line 5, after "to" insert --- a ---.

Column 3, line 28, after "of" insert --- the ---.

Column 4, line 9, before "bank" insert --- the ---.

Column 4, line 20, after "by" insert --- the ---.

Column 4, line 23, after "of" insert --- the ---.

Column 4, line 25, after "of" insert --- the ---.

Column 4, line 30, after "fills" insert --- the ---.

Column 4, line 31, after "of" insert --- the ---.

Column 4, line 32, after "of" insert --- the ---.

Column 4, line 33, after "of" insert --- the ---.

Column 4, line 35, delete "on" and insert --- for ---.

UNITED STATES PATENT AND TRADEMARK OFFICE
CERTIFICATE OF CORRECTION

PATENT NO. : 4,344,192                    Page 3 of 4

DATED : August 17, 1982

INVENTOR(S) : Jean Claude Imbert

It is certified that error appears in the above-identified patent and that said Letters Patent is hereby corrected as shown below:

Column 4, line 35, delete "27".

Column 4, line 36, delete "gauge" and insert --- gage ---.

Column 4, line 37, delete "gauge" and insert --- the gage ---.

Column 4, line 38, delete "gauge" and insert --- gage ---.

Column 4, line 39, delete "gauge" first occurence and insert --- the gage ---.

Column 4, line 39, delete "gague" second occurence and insert --- gage ---.

Column 4, line 41, after "of" insert --- the ---.

Column 4, line 41, after "27" insert --- as shown in Figure 11 ---.

UNITED STATES PATENT AND TRADEMARK OFFICE
CERTIFICATE OF CORRECTION

PATENT NO. : 4,344,192

DATED : August 17, 1982

INVENTOR(S) : Jean Claude Imbert

It is certified that error appears in the above-identified patent and that said Letters Patent is hereby corrected as shown below:

Column 4, line 42, delete "gauge" and insert

-- gage --.

Signed and Sealed this

Tenth Day of May 1983

[SEAL]

Attest:

GERALD J. MOSSINGHOFF

Attesting Officer     Commissioner of Patents and Trademarks